US006686505B2

(12) United States Patent
Watanabe et al.

(10) Patent No.: US 6,686,505 B2
(45) Date of Patent: Feb. 3, 2004

(54) PROCESS FOR PRODUCING OPTICALLY ACTIVE AMINO ALCOHOLS AND INTERMEDIATES THEREFORE

(75) Inventors: Masahito Watanabe, Saitama (JP); Kunihiko Murata, Saitama (JP); Takao Ikariya, Tokyo (JP)

(73) Assignee: Kanto Kaguku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/285,164

(22) Filed: Oct. 31, 2002

(65) Prior Publication Data

US 2003/0171592 A1 Sep. 11, 2003

(30) Foreign Application Priority Data

Oct. 31, 2001 (JP) .................................. 2001-335322
Aug. 29, 2002 (JP) .................................. 2002-251994

(51) Int. Cl.$^7$ ............................................. C07C 213/02
(52) U.S. Cl. ........................ 564/356; 564/355; 564/357; 564/358
(58) Field of Search ................................ 564/355, 356, 564/357, 358

(56) References Cited

U.S. PATENT DOCUMENTS

| 5,763,688 A | 6/1998 | Ikariya et al. ............... 568/814 |
| 6,184,381 B1 | 2/2001 | Ikariya et al. .............. 546/136 |
| 6,187,956 B1 * | 2/2001 | Klinger et al. .............. 564/358 |

FOREIGN PATENT DOCUMENTS

| EP | 1174426 A | 1/2002 |
| JP | 08-225466 A | 9/1996 |
| JP | 09-157196 A | 6/1997 |
| JP | 11-189600 A | 7/1999 |
| JP | 11-322649 A | 11/1999 |
| WO | WO 00/07976 A1 | 2/2000 |
| WO | WO 00/59885 A1 | 12/2000 |

OTHER PUBLICATIONS

Noyori R., Hashiguchi S.: "Asymmetric Transfr Hydrogenation Catalyzed by Chiral Ruthenium Complexes" Accounts of Chemical Research, vol. 30, No. 2, 1997, pp. 97–102 (XP002229949).
Solladie–Cavallo A., et al., "Asymmetric Synthesis of Ephedrine Analogs" Journal or Organometallic Chemistry, vol. 330, No. 3, Aug. 25, 1997, pp. 357–363 (XP009005021).
Watanabe M. et al., "Practical Synthesis of Opticallyb Active Amino Alcohols via Asymmetric Transfer Hydrogenation of functionalized Aromatic Ketones" Journal of Organic Chemistry, vol. 67, No. 5, Feb. 8, 2002, pp. 1712–1715 (XP002229950).
J.S. Yadav et al., "A facile synthesis of (R)–(–)–2–azido–1–arylethanols from 2–azido–1–arylketones using baker's yeast," *Tetrahedron: Asymmetry*, Jan. 9, 2001, pp. 63–67, vol. 12, Elsevier Science Ltd.

A. Kawamoto et al., "Enantioselective synthesis of β–hydroxy amines aziridines using asymmetric transfer hydrogenation of α–amido ketones," *Tetrahedron: Asymmetry*, Aug. 8, 2000, pp. 3257–3261, vol. 11, Elsevier Science Ltd.
T. Ohkuma et al., "Comprehensive Asymmetric Catalysis," *I. Springer*, 1999, pp. 210–213.
Y. Gao et al., "Asymmetric Synthesis of BOth Enantiomers and Tomoxetine and Fluoxetine, Selective Reduction of 2,3–Epoxycinnamyl Alcohol with Red–A1," *J. Org. Chem.*, Feb. 16, 1988, pp. 4081–4084, vol. 53, No. 17, American Chemical Society, USA.
E.J. Corey et al., "Enantioselective and Practical Syntheses of R–and S–Fluoxetines," *Tetrahedron Letters*, 1989, pp. 5207–5210, vol. 30, No. 39, Pergamon Press plc, GB.
S. Sakuraba et al., "Practical Asymmetric Synthesis of (R)–Fluoxetine Hydrochloride Catalyzed by (2S, 4S)–4–Dicyclohexylphosphino–2–diphenylphosphinomethyl–1–(N–methylcarbamoyl)pyrrolidine–Rhodium Complex," *Synlett*, Sep. 1991, pp. 689–690.
D. Mitchell et al., "Synthesis of R–and S–Fluoxetine, Norfluoxetine and Related Compounds from Styrene Oxide," *Synthetic Communications*, 1995, pp. 1231–1238, vol. 25, No. 8, Marcel Dekker, Inc.
T.M. Koenig et al., "A Convenient Method for Preparing Enantiomerically Pure Norfluoxetine, Fluoxetine and Tomoxetine," *Tetrahedron Letters*, 1994, pp. 1339–1342, vol. 35, No. 9, Elsevier Science Ltd., GB.
J.R. Dehli et al., "Enantio– and chemoselective bioreduction of β–keto nitriles by the fungus *Curvularia lunata*," *Tetrahedron: Asymmetry*, Sep. 1, 2000, pp. 3693–3700, vol. 11, Elsevier Science Ltd., GB.
S. Murahashi et al., "Ruthenium–Catalyzed Aldol and Michael Reactions of Nitriles. Carbon–Carbon Bond Formation by α–C–H Activation of Nitriles," *J. Am. Chem. Soc.*, 1995, pp. 12436–12451, vol. 117, No. 50, American Chemical Society, USA.
S. Hashiguchi et al., "Asymmetric Transfer Hydrogenation of Aromatic Ketones Catalyzed by Chiral Ruthenium(II) Complexes," *J. Am. Chem. Soc.*, 1995, pp. 7562–7563, vol. 117, No. 28, American Chemical Society, USA.
K. Haack et al., "The Catalyst Precursor, Catalyst, and Intermediate in the Ru$^{II}$–Promoted Asymmetric Hydrogen Transfer between Alcohols and Ketones," *Agnew. Chem. Int. Ed. Engl.*, 1997, pp. 285–288, vol. 36, No. 3, VCH Verlagsgesellschaft mbH, Germany.

* cited by examiner

*Primary Examiner*—Peter O'Sullivan
(74) *Attorney, Agent, or Firm*—Wolf, Greenfield & Sacks, P.C.

(57) ABSTRACT

A process for producing an optically active amino alcohol is provided that includes a step in which a nitro ketone or a cyano ketone is reacted with a hydrogen-donating organic or inorganic compound in the presence of a transition metal compound catalyst having an optically active nitrogen-containing compound as an asymmetric ligand to give an optically active nitro alcohol or an optically active cyano alcohol, and a step in which the above optically active alcohol is further reduced to efficiently produce an optically active amino alcohol.

11 Claims, No Drawings

PROCESS FOR PRODUCING OPTICALLY ACTIVE AMINO ALCOHOLS AND INTERMEDIATES THEREFORE

RELATED APPLICATIONS

Foreign priority benefits are claimed under 35 U.S.C. §119(a)–(d) of Japanese patent application no. 2001-335322 filed on Oct. 31, 2001; and Japanese patent application no. 2002-251994 filed on Aug. 29, 2002.

FIELD TO WHICH THE INVENTION PERTAINS

The present invention relates to a process for producing an optically active amino alcohol from a nitro ketone or a cyano ketone with a high reaction yield and high optical purity, the optically active amino alcohol being useful as a synthetic intermediate for pharmaceuticals, agrochemicals, catalysts for asymmetric synthesis, etc., and also to a process for producing an optically active nitro alcohol or an optically active cyano alcohol, which are intermediates in the production of the optically active amino alcohol.

BACKGROUND OF THE INVENTION

Optically active β-amino alcohols are important compounds as synthetic intermediates for pharmaceuticals, agrochemicals, catalysts for asymmetric synthesis, etc., and with regard to the pharmaceuticals, for example, they are important as pharmaceutical intermediates for β-adrenergic blockers.

From the point of view of safety, efficacy, etc., it is extremely important for an optically active pharmaceutical to have high optical purity and there is therefore a strong desire for the establishment of a process for producing optically active bulk pharmaceuticals or intermediates with a high reaction yield as well as high optical purity.

With regard to conventional processes for producing optically active β-amino alcohols, there are known, for example, (1) a process in which an α-azido ketone is asymmetrically reduced using bread yeast and the azido group of the β-azido alcohol thus obtained is reduced (J. S. Yadav, P. T. Reddy, S. Nanda, and A. B. Rao, Tetrahedron: Asymmetry, 12, 63 (2001)), (2) a process in which an β-amido ketone is asymmetrically reduced using a metal catalyst to give a β-amido alcohol, and aprotecting group on the nitrogen is removed (A. Kawamoto and M. Wills, Tetrahedron: Asymmetry, 11, 3257(2000)), and (3) a process in which an β-amino ketone is asymmetrically reduced using a metal catalyst (Comprehensive Asymmetric Catalysis, I. Springer, p. 210–212 (1999)).

Among the processes described above, process (1) has the defects that the type of reaction substrate is restricted and, moreover, the absolute configuration of the alcohol so obtained is limited to a specific type. In process (2), the yield when removing the protecting group on the nitrogen is low and it is not suitable for industrial production. Process (3) cannot always be said to have generality since the type of a suitable substrate depends on the type of a metal catalyst. Furthermore, the type of substituent on the nitrogen is restricted, and it lacks versatility.

On the other hand, there is no known process that can produce a β-amino alcohol by forming an optically active β-nitro alcohol derivative from an α-nitro ketone by asymmetric reduction using a metal catalyst, and further reducing the intermediate thus obtained.

Optically active γ-amino alcohols are important compounds as optically active pharmaceutical intermediates and are synthetic intermediates for, for example, fluoxetine, which is known as an antidepressant. There are various known processes for producing optically active γ-amino alcohols. A process in which cinnamyl alcohol is subjected to Sharpless oxidation to give optically active 2,3-epoxycinnamyl alcohol, this is reduced with Red-Al to give the 1,3-diol, the 1-position is mesylated, and it is then reacted with an amine (Y. Gao and K. B. Sharpless, J. Org. Chem., 53, 4081 (1988)), and a process in which 3-chloropropiophenone is subjected to borane reduction in the presence of an optically active oxazaborolidine to give optically active 3-chloro-1-phenylpropanol, which is subsequently treated with sodium iodide and then reacted with an amine (E. J. Corey and G. A. Reichard, Tetrahedron Lett., 30, 5207 (1989)) have the problem that since large amounts of optically active material and reducing agent are required, the economic efficiency is poor, and the production cost is high.

In a process for obtaining an optically active γ-amino alcohol by asymmetric hydrogenation of a β-amino ketone hydrochloride with MCCPM-Rh catalyst (S. Sakuraba and K. Achiwa, Synlett, 689 (1991)), there is the problem that the γ-amino alcohol thus obtained has low optical purity. In a process in which an optically active β-cyano alcohol is obtained by a reaction between optically active styrene oxide and acetone cyanohydrin, and the cyano group is then reduced (D. Mitchell and T. M. Koenig, Synthetic Communications, 25, 1231 (1995)), since large amounts of optically active material and highly toxic compounds are required, it is not suitable for industrial production in terms of cost and safety. In a process in which a β-cyano alcohol racemate is synthesized by a reaction between benzaldehyde and acetonitrile, and the cyano group is further reduced to give a γ-amino alcohol, which is then optically resolved to give an optically active γ-amino alcohol(T. M. Koenig and D. Mitchell, Tetrahedron Lett., 35, 1339 (1994)), optical resolution, which is a very complicated operation, is required in order to obtain an optically active material, and there is also the defect that, since the starting material is used after optical resolution, half of the starting material is wasted.

With regard to a process for producing an optically active β-cyano alcohol by asymmetric reduction of benzoylacetonitrile, which is an α-cyano ketone, there is a process in which the asymmetric reduction is carried out by a microorganism (J. R. Dehli and V. Gotor, Tetrahedron: Asymmetry, 11, 3693 (2000)). This process has the defects that the reaction yield is low and the absolute configuration of the alcohol so obtained is limited to a specific type.

With regard to the production of an optically active amino alcohol from a cyano ketone using a metal catalyst, a borane reduction process (using an optically active oxazaborolidine as a catalyst) is only disclosed in WO 00/07976, but this process has the problem of borane liquid waste since the borane compound and the cyano ketone are used in equimolar amounts.

With regard to a process for reducing a ketone to an alcohol using a transition metal complex, various techniques have been proposed. JP, A, 8-225466 discloses a hydrogen reduction process using an optically active phosphine and an optically active amine as ligands of a transition metal complex, and JP, A, 11-189600 relates to a process for producing an optically active alcohol from a carbonyl compound using a novel ruthenium complex having phosphine and amine ligands, etc. Furthermore, JP, A, 9-157196 and JP, A, 11-322649 disclose reactions of transition metal complexes having as a ligand an optically active nitrogen-containing compound using a hydrogen donor compound instead of hydrogen. JP, A, 9-157196 illustrates as reaction substrates a large number of carbonyl compounds having as one or more substituents an aromatic compound, a heterocyclic compound, an aliphatic compound, etc., and although they include carbonyl compounds substituted with a cyano group, which is electron-withdrawing and shows strong coordination to a transition metal, or a nitro group, which is electron-withdrawing, in the embodiments there is no mention of a reaction for their reduction into a cyano alcohol or a nitro alcohol using as a substrate a cyano ketone or a nitro ketone having a cyano or nitro group on the α-carbon, and neither is there mention of other cyano ketones and nitro ketones.

Furthermore, WO 00/59885 discloses a process for producing a specific tricyclic amino alcohol derivative, etc. in which (R)-2-azido-1-(4-benzyloxy-3-methylsulfonyl amino)phenylethanol is synthesized by a hydrogen-transfer type asymmetric reduction of 2-azido-1-(4-benzyloxy-3-methylsulfonylamino)phenylethanone, but it cannot be predicted that α-nitro ketones and α-cyano ketones will react in the same manner.

In general, a reaction using a metal catalyst is greatly affected by the structure of the substrate, and in particular the type of the functional group present in the molecule.

The reaction of a compound having a strongly electron-withdrawing nitro group cannot be considered in the same manner as the reaction of a compound having an azido group. For example, a hydrogen of nitromethane, which has a nitro group, has a pKa of 11, indicating that its acidity is comparatively high, and deprotonation thereof by a base proceeds easily. In a hydrogen-transfer type asymmetric reduction of a ketone carried out in the presence of a base, it is therefore surmised that the reaction of a ketone substituted with a nitro group at the α-position will be more strongly inhibited compared with a compound substituted with an azido group.

A cyano group is less electron withdrawing than a nitro group but more electron withdrawing than an azido group. Furthermore, the cyano group shows strong coordination to a transition metal. Taking advantage of these properties, a Michael reaction and an aldol reaction using a compound having a cyano group as a donor have been developed, but there have been no reports of a similar reaction using an azido compound (S. Murahashi et al., J. Am. Chem. Soc., 117, 12436 (1998)). Because of this, when attempting to carry out asymmetric reduction of a ketone having a cyano group at the α-position using a transition metal complex, it is surmised that the catalytic reaction will be inhibited both in terms of the strong electron-withdrawing properties of the cyano group and the strong coordination to the transition metal.

In this way, with regard to the reactions using a metal catalyst, it is surmised that nitro ketones and cyano ketones will behave as substrates having completely different properties from those of azido ketones.

SUMMARY OF THE INVENTION

In view of the above-mentioned circumstances, it is therefore an object of the present invention to provide a process for efficiently producing an optically active amino alcohol by producing an optically active nitro alcohol or an optically active cyano alcohol with a high reaction yield and high optical purity from a nitro ketone or a cyano ketone by hydrogen-transfer type asymmetric reduction using a catalytic amount of a source of asymmetry, and further reducing the product.

As a result of an intensive investigation by the present inventors in order to achieve the above-mentioned object, it has been found that an optically active amino alcohol can be obtained by forming an optically active nitro alcohol derivative or an optically active cyano alcohol derivative from a nitro ketone or a cyano ketone with high reaction yield and high optical purity by hydrogen-transfer type asymmetric reduction using an optically active nitrogen-containing compound, a compound of a metal belonging to group VIII of the periodic table, a hydrogen donor, and a base, and further reducing the intermediate thus obtained, and the present invention has thus been accomplished.

In general, nitro ketones and cyano ketones have an activated methylene group due to the presence of the strongly electron-withdrawing group in the molecule, and this activated methylene group is susceptible to a nucleophilic reaction with a carbonyl carbon under basic conditions, thus causing side reactions such as a condensation reaction between molecules in these compounds. α-Nitro ketones and α-cyano ketones in particular have a highly acidic hydrogen on the methylene carbon activated by the two strongly electron-withdrawing groups in the molecule. It is surmised that treatment with a base therefore easily converts them into the enolate anion, and the nucleophilic reaction with the carbonyl carbon thereby proceeds easily.

The present inventors themselves therefore expected that, in the hydrogen-transfer type asymmetric reduction reaction using a base, particularly when an α-nitro ketone or an α-cyano ketone is used, side reactions such as condensation reactions between the carbonyl compounds would occur to a great extent, and did not think that the corresponding optically active nitro alcohol or cyano alcohol would be produced efficiently. In fact, when an α-nitro ketone is subjected to asymmetric reduction under the reaction conditions in an example of JP, A, 9-157196 above, side reactions such as condensation reactions between the substrate molecules were observed to a great extent, and the target product could either not be obtained or the yield was low.

Judging from this result, it is surprising that an amino alcohol can be produced by the above-mentioned process, and this process enables the extremely efficient production of an amino alcohol without any restriction on the absolute configuration of the alcohol, and the present invention is extremely significant for the industrial production of amino alcohols.

That is, the present invention relates to a process for producing an optically active amino alcohol that includes a step in which a compound represented by general formula (A)

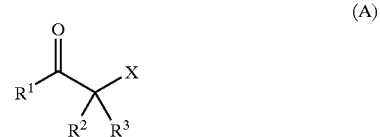

(A)

(in the formula, $R^1$ is an aromatic monocyclic or aromatic polycyclic hydrocarbon group, which may have one or more substituents, a saturated or unsaturated aliphatic hydrocarbon or alicyclic hydrocarbon group, which may have one or more substituents, or a heteromonocyclic or heteropolycyclic group, which may have one or more substituents, $R^2$ and $R^3$ each independently denote a hydrogen atom, a halogen atom, a carboxyl group, a hydroxyl group, an alkoxy group, an aromatic monocyclic or aromatic polycyclic hydrocarbon group, which may have one or more substituents, a saturated or unsaturated aliphatic hydrocarbon or alicyclic hydrocarbon group, which may have one or more substituents and which may contain a heteroatom, or a heteromonocyclic or heteropolycyclic group, which may have one or more substituents, any two of $R^1$ to $R^3$ may bond together so as to form a ring, and X denotes a nitro group or a cyano group)

is reacted, in the presence or absence of a base, with an optically active nitrogen-containing compound, a compound of a metal belonging to group VIII of the periodic table, and a hydrogen donor so as to obtain a compound represented by general formula (B)

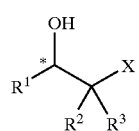

(B)

(in the formula, $R^1$, $R^2$, $R^3$, and X are as defined above, and * denotes an asymmetric carbon atom)

from the compound represented by general formula (A) and a step in which a compound represented by general formula (C)

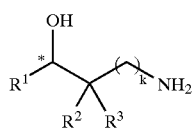

(C)

(in the formula, $R^1$, $R^2$, and $R^3$ are as defined above, k denotes an integer of 0 or 1 and * denotes an asymmetric carbon atom)

is obtained from the compound represented by general formula (B).

Furthermore, the present invention relates to the above-mentioned process for producing an optically active amino alcohol wherein, in the step in which the compound represented by general formula (B) is obtained from the compound represented by general formula (A), the compound represented by general formula (B) is obtained by reacting the compound represented by general formula (A), in the presence or absence of a base, with the hydrogen donor and a complex prepared in advance from the optically active nitrogen-containing compound and the compound of a metal belonging to group VIII of the periodic table.

Moreover, the present invention relates to the above-mentioned process for producing an optically active amino alcohol wherein the optically active nitrogen-containing compound is a compound represented by general formula (D).

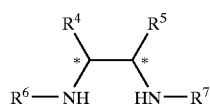

(D)

(In the formula, $R^4$ and $R^5$ each independently denote an aromatic monocyclic or aromatic polycyclic hydrocarbon group, which may have one or more substituents, a saturated or unsaturated aliphatic hydrocarbon or alicyclic hydrocarbon group, which may have one or more substituents and which may contain a heteroatom, or a heteromonocyclic or heteropolycyclic group, which may have one or more substituents, $R^4$ and $R^5$ may bond together so as to form a ring, $R^6$ and $R^7$ each independently denote a hydrogen atom, a lower alkyl group, an acyl group, a carbamoyl group, a thioacyl group, a thiocarbamoyl group, an alkylsulfonyl group, or an arylsulfonyl group and

* denotes an asymmetric carbon atom.)

Furthermore, the present invention relates to the above-mentioned process for producing an optically active amino alcohol wherein the optically active nitrogen-containing compound is a compound represented by general formula (E).

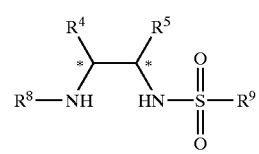

(E)

(In the formula, $R^4$ and $R^5$ are as defined above, $R^8$ denotes a hydrogen atom or an alkyl group, $R^9$ denotes an alkyl or aryl group, which may have one or more substituents and

* denotes an asymmetric carbon atom.)

Moreover, the present invention relates to the above-mentioned process for producing an optically active amino alcohol wherein the optically active nitrogen-containing compound is a compound represented by general formula (F).

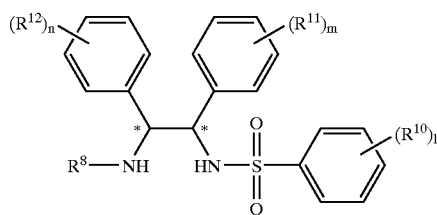

(F)

(In the formula, $R^8$ is as defined above, $R^{10}$, $R^{11}$, and $R^{12}$ each independently denote a hydrogen atom, a lower alkyl group, a halogen atom, or a lower alkoxy group, l, m, and n each independently denote an integer of 1 to 5, and

* denotes an asymmetric carbon atom.)

Furthermore, the present invention relates to the above-mentioned process for producing an optically active amino alcohol wherein the compound of a metal belonging to group VIII of the periodic table is a ruthenium compound.

Moreover, the present invention relates to the above-mentioned process for producing an optically active amino alcohol wherein the hydrogen donor is one or more compounds selected from the group consisting of formic acid, formates, and alcohol compounds, and the base is one or more compounds selected from the group consisting of organic amines, alkali metal hydroxides, and alkali metal alkoxides.

Furthermore, the present invention relates to the above-mentioned process for producing an optically active amino alcohol wherein the hydrogen donor is formic acid, and the base is a tertiary amine.

Moreover, the present invention relates to the above-mentioned process for producing an optically active amino alcohol wherein the step in which the compound represented by general formula (C) is obtained from the compound represented by general formula (B) is a reduction step involving a reaction with hydrogen in the presence of a heterogeneous metal catalyst or a reduction step involving a reaction with a metal hydride or a boron hydride compound.

Furthermore, the present invention relates to the above-mentioned process for producing an optically active amino alcohol wherein X is a nitro group and in the step in which the compound represented by general formula (B) is obtained from the compound represented by general formula (A) a reaction solvent is further added.

Moreover, the present invention relates to a use of the above-mentioned process for producing an optically active amino alcohol in order to produce fluoxetine, tomoxetine, nisoxetine, norfluoxetine or a derivative thereof.

MODES FOR CARRYING OUT THE INVENTION

Compounds that can be used as starting materials in the present invention are nitro ketones and cyano ketones represented by general formula (A).

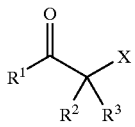
(A)

In general formula (A), $R^1$ is an aromatic monocyclic or aromatic polycyclic hydrocarbon group, which may have one or more substituents, a saturated or unsaturated aliphatic hydrocarbon or alicyclic hydrocarbon group, which may have one or more substituents, or a heteromonocyclic or heteropolycyclic group, which may have one or more substituents, $R^2$ and $R^3$ each independently denote a hydrogen atom, a halogen atom, a carboxyl group, a hydroxyl group, an alkoxy group, an aromatic monocyclic or aromatic polycyclic hydrocarbon group, which may have one or more substituents, a saturated or unsaturated aliphatic hydrocarbon or alicyclic hydrocarbon group, which may have one or more substituents and which may contain a heteroatom or a heteromonocyclic or heteropolycyclic group, which may have one or more substituents, any two of $R^1$ to $R^3$ may bond together so as to form a ring, and X denotes a nitro group or a cyano group.

The heteroatom referred to above denotes a nitrogen atom, an oxygen atom, a sulfur atom, etc. in an organic compound.

Specific examples of the aromatic monocyclic hydrocarbon group include phenyl, 2-methylphenyl, 2-ethylphenyl, 2-isopropylphenyl, 2-tert-butylphenyl, 2-methoxyphenyl, to 2-chlorophenyl, 2-vinylphenyl, 3-methylphenyl, 3-ethylphenyl, 3-isopropylphenyl, 3-methoxyphenyl, 3-chlorophenyl, 3-vinylphenyl, 4-methylphenyl, 4-ethylphenyl, 4-isopropylphenyl, 4-tert-butylphenyl, 4-vinylphenyl, mesityl and xylyl.

Furthermore, specific examples of the aromatic polycyclic hydrocarbon group include 1-naphthyl, 2-naphthyl, anthryl, phenanthryl and indenyl.

Specific examples of the heteromonocyclic group include thienyl, furyl, pyranyl, pyrrolyl, imidazolyl, pyrazolyl, oxazolyl, isooxazolyl, triazolyl, thiazolyl, isothiazolyl, pyridyl, pyradazyl and pyrazinyl.

Furthermore, specific examples of the heteropolycyclic group include benzoimidazolyl, benzopyrazolyl, benzothiazolyl, quinolyl, anthranyl, indolyl and phenanthronilyl.

The aliphatic hydrocarbon group is a straight-chain or branched-chain alkyl, alkenyl, or alkynyl group, which may be substituted with an aromatic hydrocarbon group or an aromatic heterocyclic group.

With regard to examples of the alkyl group, there can be cited alkyl groups having 1 to 20 carbons such as methyl, ethyl, n-propyl, isopropyl, butyl, sec-butyl, tert-butyl, pentyl, isopentyl, neopentyl, tert-pentyl, hexyl, heptyl, octyl, nonyl, decyl and dodecyl.

With regard to examples of the alkenyl group, there can be cited alkenyl groups having 2 to 20 carbons such as vinyl, 1-propenyl, 2-propenyl, 1-butenyl, isopropenyl, 2-butenyl, 3-butenyl, 1,3-butadienyl, 1-pentenyl, 2-pentenyl and 3-pentenyl.

With regard to examples of the alkynyl group, there can be cited alkynyl groups having 2 to 20 carbons such as acetylenyl, methylacetylenyl and phenylacetylenyl.

The alicyclic hydrocarbon group denotes a cycloalkyl group, which may be substituted with an aromatic hydrocarbon group or an aromatic heterocyclic group, and specific examples thereof include cycloalkyl groups having 3 to 8 carbons such as cyclopropyl, cyclobutyl, cyclopentyl and cyclohexyl.

With regard to substituents that bond to these aromatic hydrocarbon groups, aromatic heterocyclic groups, aliphatic hydrocarbon groups or alicyclic hydrocarbon groups, there can be cited as specific examples halogen atoms such as fluorine, chlorine, bromine, and iodine; halogen-containing hydrocarbon groups such as a trifluoromethyl group, oxygen-containing substituents such as hydroxyl, alkoxy, acyl, alkoxycarbonyl and carboxyl groups; nitrogen-containing substituents such as amino, alkylamino, nitro, cyano and azido groups; silicon-containing substituents such as trimethylsilyl and hydrosilyl groups; sulfur-containing substituents such as mercapto and alkylthio groups; and phosphorus-containing substituents such as phosphoryl and triphenylphosphinyl groups. Specific examples of one or more substituents containing a transition metal element include iron-containing substituents such as a ferrocenyl group.

Moreover, any two of $R^1$ to $R^3$ may bond together by condensation and become a trimethylene, tetramethylene, pentamethylene, methylene dioxy group, etc. so as to form a ring. X denotes a nitrogen-containing substituent and specific examples thereof include a nitro group and a cyano group.

Among compounds represented by general formula (A), specific examples of the nitro ketones are shown in Compound Group 1, and nitro ketones having an aromatic hydrocarbon group or a heterocyclic hydrocarbon group represented by 1–12 and 23–29 in Compound Group 1 are particularly preferred because of their wide applicability and so forth. The nitro ketones of general formula (A), however, are not limited to the compounds of Compound Group 1.

Compound Group 1
1
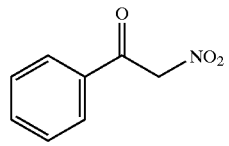
2
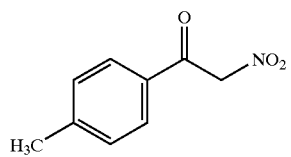
3
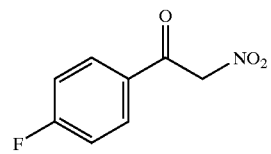
4
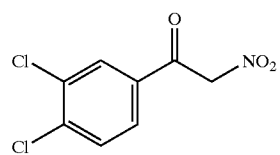
5
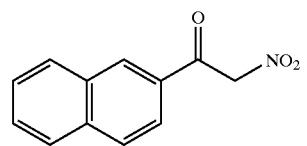
6
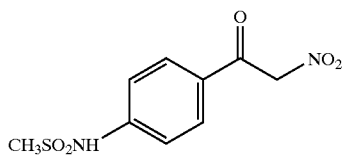
7
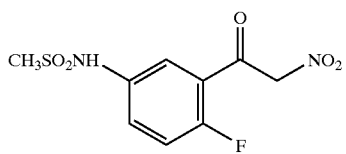
8
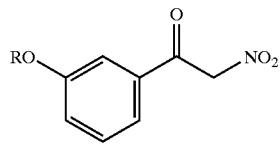
9
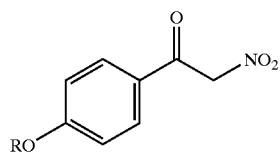
-continued
10
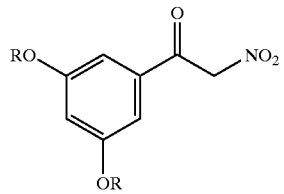
11
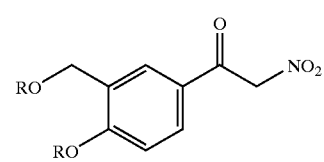
12
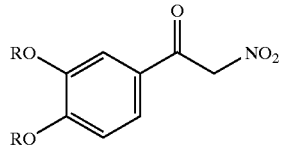
13
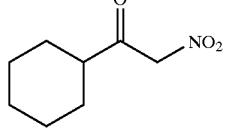
14
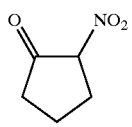
15
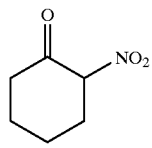
16
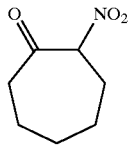
17
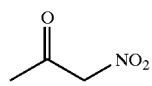
18
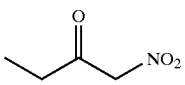
19
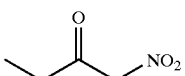
20
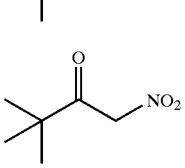

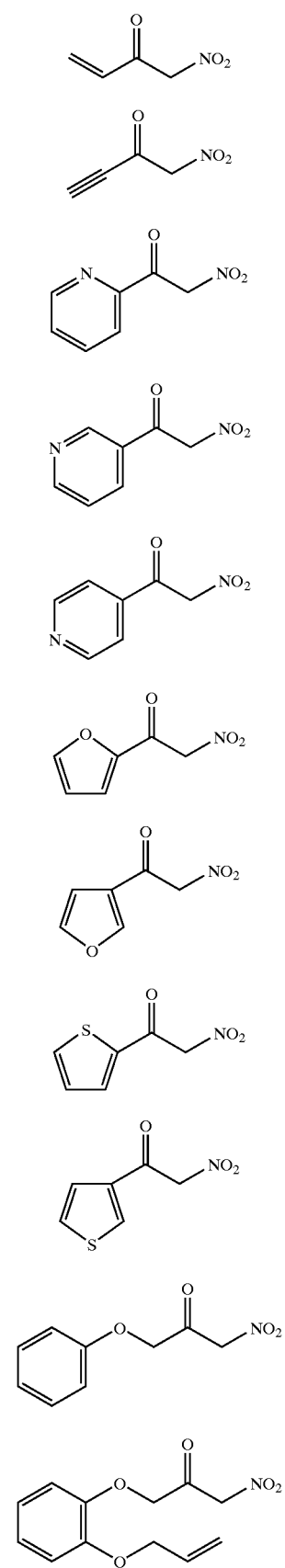
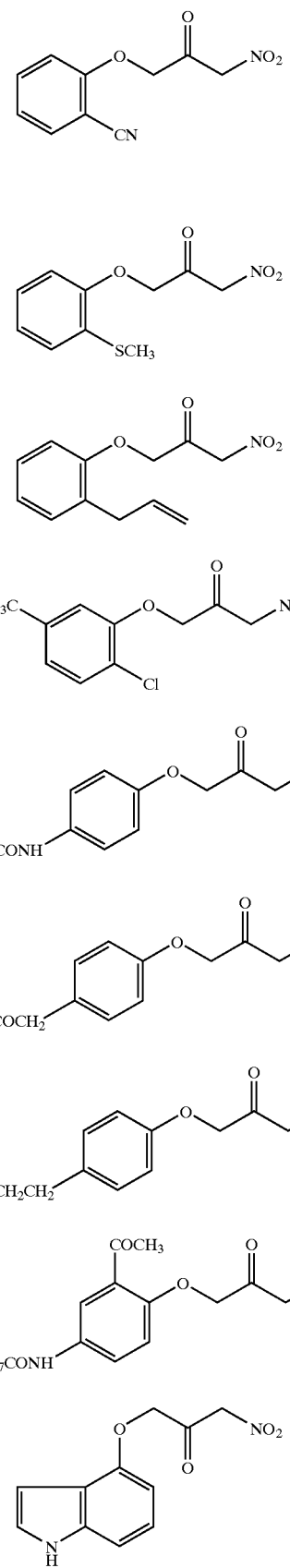

In the formulae of Compound Group 1, R denotes hydrogen, methyl, tetrahydropyranyl, allyl, isopropyl, tert-butyl, benzyl, acetyl, trimethylsilyl, tert-butyldimethylsilyl, etc.

Among compounds represented by general formula (A), specific examples of the cyano ketones are shown in Compound Group 2, and cyano ketones having an aromatic hydrocarbon group or a heterocyclic hydrocarbon group represented by 1–12 and 23–29 in Compound Group 2 are particularly preferred because of their wide applicability and so forth. The cyano ketones of general formula (A), however, are not limited to the compounds of Compound Group 2.

Compound Group 2

-continued
13 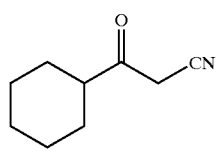
14 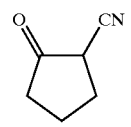
15 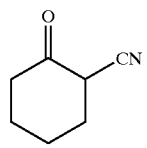
16 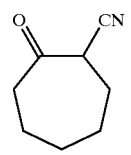
17 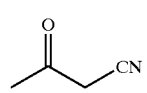
18 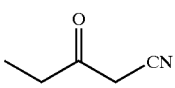
19 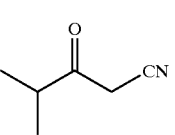
20 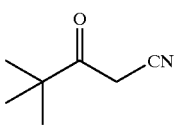
21 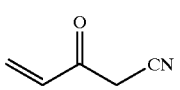
22 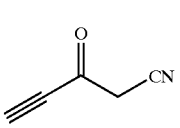
23 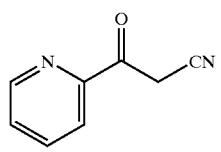
24 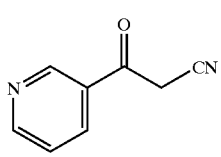
-continued
25 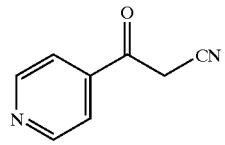
26 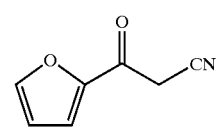
27 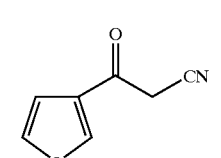
28 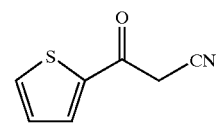
29 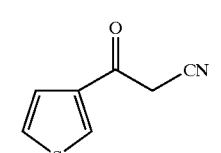
30 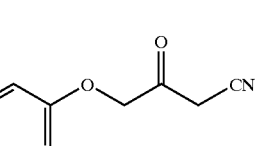
31 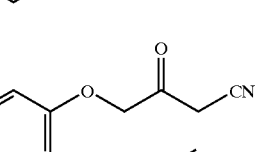
32 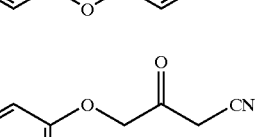
33 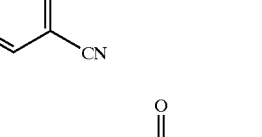
34 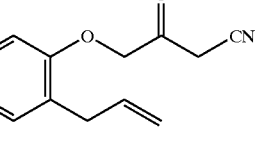

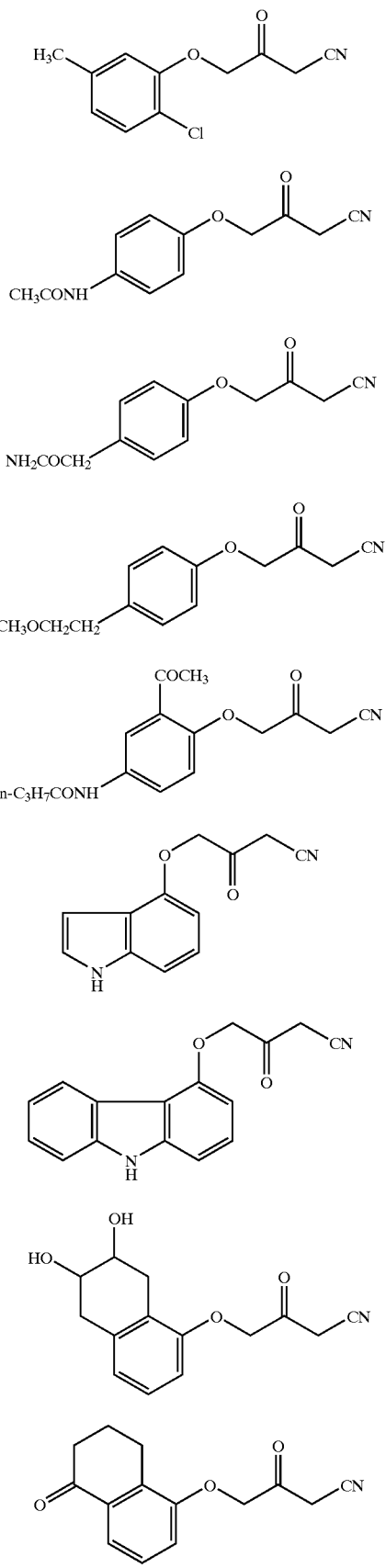

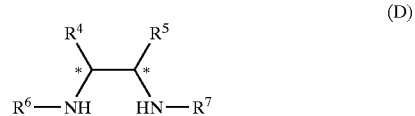

In the formulae of Compound Group 2, R denotes hydrogen, methyl, tetrahydropyranyl, allyl, isopropyl, tert-butyl, benzyl, acetyl, trimethylsilyl, tert-butyldimethylsilyl, etc.

The optically active nitrogen-containing compound, which forms a catalyst used in the present invention, is a diamine derivative represented by general formula (D).

$$\underset{R^6-NH\quad HN-R^7}{\overset{R^4\quad R^5}{\underset{*\quad *}{\diagdown\diagup}}}\tag{D}$$

In general formula (D), $R^4$ and $R^5$ independently denote an aromatic monocyclic or aromatic polycyclic hydrocarbon group, which may have one or more substituents, a saturated or unsaturated aliphatic hydrocarbon or alicyclic hydrocarbon group, which may have one or more substituents and which may contain a heteroatom or a heteromonocyclic or heteropolycyclic group, which may have one or more substituents, $R^4$ and $R^5$ may bond together so as to form a ring, $R^6$ and $R^7$ each independently denote a hydrogen atom, a lower alkyl group, an acyl group, a carbamoyl group, a thioacyl group, a thiocarbamoyl group, an alkylsulfonyl group or an arylsulfonyl group and

* denotes an asymmetric carbon atom.

Specific examples of $R^4$ and $R^5$ include straight-chain or branched-chain alkyl groups having 1 to 6 carbons such as methyl, ethyl, n-propyl, isopropyl, butyl, sec-butyl, tert-butyl, pentyl, isopentyl, neopentyl, tert-pentyl and hexyl; aryl groups such as phenyl, naphthyl, 4-methylphenyl, 3,5-dimethylphenyl, and 4-methoxyphenyl; and aromatic heterocyclic groups such as furyl and pyridyl.

Furthermore, $R^4$ and $R^5$ may together form a tetramethylene group (forming a cyclohexane ring), etc. These groups may be further substituted, and the substituent is one group or two or more groups selected from lower alkyl groups such as methyl, ethyl, n-propyl, and isopropyl, lower alkoxy groups such as methoxy and ethoxy, and halogen atoms such as chlorine, bromine, and fluorine. $R^4$ and $R^5$ are preferably phenyl, substituted phenyl, etc.

$R^6$ and $R^7$ are each independently hydrogen atoms, straight-chain or branched-chain lower alkyl groups having 1 to 6 carbons such as methyl, ethyl, n-propyl and isopropyl, acyl groups such as acetyl, propionyl and benzoyl, carbamoyl groups such as N-methylcarbamoyl and N-phenylcarbamonyl, thioacyl groups such as thioacetyl, thiopropionyl and thiobenzoyl, thiocarbamonyl groups such as N-methylthiocarbamoyl and N-phenylthiocarbamoyl, and alkylsulfonyl or arylsulfonyl groups having 1 to 20 carbons, which may be substituted, such as methanesulfonyl, ethanesulfonyl, benzenesulfonyl, 2,4,6-mesitylsulfonyl, 2,4,6-triisopropylbenzenesulfonyl, 4-methoxybenzenesulfonyl, 4-chlorobenzenesulfonyl and p-toluenesulfonyl. It is preferable for at least one of $R^6$ and $R^7$ to be a hydrogen atom. More preferably, one of $R^6$ and $R^7$ is an arylsulfonyl group and, in particular, p-toluenesulfonyl.

The optically active nitrogen-containing compound forming a catalyst used in the present invention is preferably a diamine derivative represented by general formula (E).

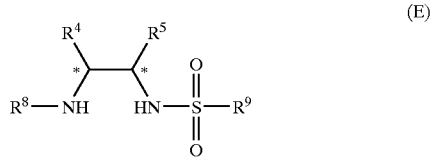

(In the formula, $R^4$ and $R^5$ are as defined above,
$R^8$ denotes a hydrogen atom or an alkyl group,
$R^9$ denotes an alkyl or aryl group, which may have one or more substituents and
* denotes an asymmetric carbon atom.)

More preferably, the optically active nitrogen-containing compound is a diamine derivative represented by general formula (F).

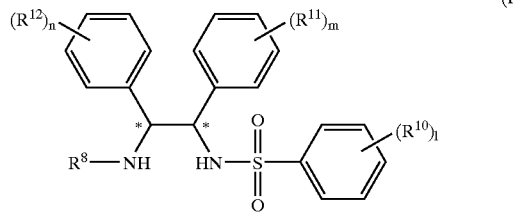

(In the formula, $R^8$ is as defined above,
$R^{10}$, $R^{11}$, and $R^{12}$ each independently denote a hydrogen atom, a lower alkyl group, a halogen atom, or a lower alkoxy group,
l, m, and n independently denote an integer of 1 to 5 and
* denotes an asymmetric carbon atom.)

Specific examples of $R^4$, $R^5$, and $R^8$ to $R^{12}$ in general formulae (E) and (F) when they denote alkyl groups, aryl groups, halogen atoms, and alkoxy groups are as defined above.

Specific examples of the optically active nitrogen-containing compounds represented by general formulae (D), (E), and (F) include 1,2-diphenylethylenediamine, N-methyl-1,2-diphenylethylenediamine, N-(p-toluenesulfonyl)-1,2-diphenylethylenediamine, N-methanesulfonyl-1,2-diphenylethylenediamine, N-methyl-N'-(p-toluenesulfonyl)-1,2-diphenylethylenediamine, N-p-methoxyphenylsulfonyl-1,2-diphenylethylenediamine, N-p-chlorophenylsulfonyl-1,2-diphenylethylenediamine, N-p-mesitylsulfonyl-1,2-diphenylethylenediamine, and N-(2,4,6-triisopropyl)phenylsulfonyl-1,2-diphenylethylenediamine.

With regard to the types of metal in the compounds of a metal belonging to group VIII of the periodic table that are used in combination with the optically active nitrogen-containing compounds above, there can be cited as examples ruthenium, rhodium, iridium, cobalt, iron, nickel, palladium, platinum, and osmium, and among these ruthenium is preferred.

Specific compounds include $RuCl_3\cdot3H_2O$, $[RuCl_2(p\text{-cymene})]_2$, $[RuCl_2(benzene)]_2$, $[RuCl_2(mesitylene)]_2$, $[RuCl_2(hexamethylbenzene)]_2$, $RuCl_2(PPh_3)_3$, $[RuCl_2(cod)]_n$, $[RuCl_2(CO)_3]_2$, $[Rh(cod)Cl]_2$, $[RhCl_2(pentamethylcyclopentadienyl)]_2$, $[Ir(cod)Cl]_2$, $CoCl_2$, $NiCl_2$, $NiBr_2$, $NiCl_2(PPh_3)_2$, $NiBr_2(PPh_3)_2$, $PdCl_2$, $Pd(PPh_3)_4$, $PdCl_2(CH_3CN)_2$, $PdCl_2(PhCN)_2$, $PtCl_2(cod)$, and $Pt(PPh_3)_4$ etc. and preferably $[RuCl_2(p\text{-cymene})]_2$, $[RuCl_2(benzene)]_2$, $[RuCl_2(mesitylene)]_2$, and $[RuCl_2(hexamethylbenzene)]_2$. In the above-mentioned compounds Ph denotes a phenyl group and cod denotes cyclooctadiene.

The present invention includes two steps: (1) a step in which an asymmetric reduction reaction is carried out on nitro ketones or cyano ketones, and (2) a step in which an optically active nitro alcohols or cyano alcohols are reduced.

Step (1) Asymmetric Reduction Reaction of Nitro Ketones and Cyano Ketones

The asymmetric reduction step of the present invention is carried out by bringing a starting material into contact with a hydrogen donor, a compound of a metal belonging to group VIII of the periodic table and an optically active nitrogen-containing compound in the presence or absence of a base. The compound of a metal belonging to group VIII of the periodic table and the optically active nitrogen-containing compound may be added to a reactor separately or, prior to carrying out an asymmetric reduction reaction, the two compounds may be subjected to a reaction so as to separately prepare a complex in which the optically active nitrogen-containing compound coordinates to the metal atom belonging to group VIII of the periodic table, said complex being used.

With regard to a specific process for synthesizing the catalyst, a known process disclosed in J. Am. Chem. Soc., 117, 7562 (1995) can be employed. For example, an optically active nitrogen-containing compound and a compound of a metal belonging to group VIII of the periodic table are heated in a solvent such as 2-propanol in the presence of a base such as triethylamine to give a diamine complex in which the optically active nitrogen-containing compound coordinates to the metal atom. This diamine complex can be used as it is or it may be isolated as crystals by a known process disclosed in Angew. Chem. Int. Ed. Engl., 36, 285 (1997).

With regard to the complex in which the optically active nitrogen-containing compound coordinates to the metal atom belonging to group VIII of the periodic table, there can be cited a chloride complex, an amide complex, a hydride complex, etc.

Specific examples of the chloride complex include chloro[(S,S)-N-(p-toluenesulfonyl)-1,2-diphenylethylene diamine]benzeneruthenium, chloro[(R,R)-N-(p-toluenesulfonyl)-1,2-diphenylethylene diamine]benzeneruthenium, chloro[(S,S)-N-(p-toluenesulfonyl)-1,2-diphenylethylene diamine](p-cymene)ruthenium, chloro[(R,R)-N-(p-toluenesulfonyl)-1,2-diphenylethylene diamine](p-cymene)ruthenium, chloro[(S,S)-N-(p-toluenesulfonyl)-1,2-diphenylethylene diamine](mesitylene)ruthenium, chloro[(R,R)-N-(p-toluenesulfonyl)-1,2-diphenylethylene diamine](mesitylene)ruthenium, chloro[(S,S)-N-(p-toluenesulfonyl)-1,2-diphenylethylene diamine](hexamethylbenzene)ruthenium, chloro[(R,R)-N-(p-toluenesulfonyl)-1,2-diphenylethylene diamine](hexamethylbenzene)ruthenium, chloro[(S,S)-N-methanesulfonyl-1,2-diphenylethylene diamine]benzeneruthenium, chloro[(R,R)-N-methanesulfonyl-1,2-diphenylethylene diamine]benzeneruthenium, chloro[(S,S)-N-methanesulfonyl-1,2-diphenylethylene diamine](p-cymene)ruthenium, chloro[(R,R)-N-methanesulfonyl-1,2-diphenylethylene diamine](p-cymene)ruthenium, chloro[(S,S)-N-methanesulfonyl-1,2-diphenylethylene diamine](mesitylene)ruthenium, chloro[(R,R)-N-methanesulfonyl-1,2-diphenylethylene diamine](mesitylene)ruthenium, chloro[(S,S)-N-methanesulfonyl-1,2-diphenylethylene diamine](hexamethylbenzene)ruthenium, and chloro[(R,R)-N-methanesulfonyl-1,2-diphenylethylene diamine](hexamethylbenzene)ruthenium.

Specific examples of the amide complex include [(S,S)-N-(p-toluenesulfonyl)-1,2-diphenylethylenediamine]benzeneruthenium, [(R,R)-N-(p-toluenesulfonyl)-1,2-diphenylethylenediamine]benzeneruthenium, [(S,S)-N-(p-toluenesulfonyl)-1,2-diphenylethylenediamine](p-cymene)ruthenium, [(R,R)-N-(p-toluenesulfonyl)-1,2-diphenylethylenediamine](p-cymene)ruthenium, [(S,S)-N-(p-toluenesulfonyl)-1,2-diphenylethylenediamine](mesitylene)ruthenium, [(R,R)-N-(p-toluenesulfonyl)-1,2-diphenylethylenediamine](mesitylene)ruthenium, [(S,S)-N-(p-toluenesulfonyl)-1,2-diphenylethylenediamine](hexamethylbenzene)ruthenium, [(R,R)-N-(p-toluenesulfonyl)-1,2-diphenylethylenediamine](hexamethylbenzene)ruthenium, [(S,S)-N-methanesulfonyl-1,2-diphenylethylenediamine]benzeneruthenium, [(R,R)-N-methanesulfonyl-1,2-diphenylethylenediamine]benzeneruthenium, [(S,S)-N-methanesulfonyl-1,2-diphenylethylenediamine](p-cymene)ruthenium, [(R,R)-N-methanesulfonyl-1,2-diphenylethylenediamine](p-cymene)ruthenium, [(S,S)-N-methanesulfonyl-1,2-diphenylethylenediamine](mesitylene)ruthenium, [(R,R)-N-methanesulfonyl-1,2-diphenylethylenediamine](mesitylene)ruthenium, [(S,S)-N-methanesulfonyl-1,2-diphenylethylenediamine](hexamethylbenzene)ruthenium, and [(R,R)-N-methanesulfonyl-1,2-diphenylethylenediamine](hexamethylbenzene)ruthenium.

Specific examples of the hydride complex include hydrido[(S,S)-N-(p-toluenesulfonyl)-1,2-diphenylethylene diamine]benzeneruthenium, hydrido[(R,R)-N-(p-toluenesulfonyl)-1,2-diphenylethylene diamine]benzeneruthenium, hydrido[(S,S)-N-(p-toluenesulfonyl)-1,2-diphenylethylene diamine](p-cymene)ruthenium, hydrido[(R,R)-N-(p-toluenesulfonyl)-1,2-diphenylethylene diamine](p-cymene)ruthenium, hydrido[(S,S)-N-(p-toluenesulfonyl)-1,2-diphenylethylene diamine](mesitylene)ruthenium, hydrido[(R,R)-N-(p-toluenesulfonyl)-1,2-diphenylethylene diamine](mesitylene)ruthenium, hydrido[(S,S)-N-(p-toluenesulfonyl)-1,2-diphenylethylene diamine](hexamethylbenzene)ruthenium, hydrido[(R,R)-N-(p-toluenesulfonyl)-1,2-diphenylethylene diamine](hexamethylbenzene)ruthenium, hydrido[(S,S)-N-methanesulfonyl-1,2-diphenylethylene diamine]benzeneruthenium, hydrido[(R,R)-N-methanesulfonyl-1,2-diphenylethylene diamine]benzeneruthenium, hydrido[(S,S)-N-methanesulfonyl-1,2-diphenylethylene diamine](p-cymene)ruthenium, hydrido[(R,R)-N-methanesulfonyl-1,2-diphenylethylene diamine](p-cymene)ruthenium, hydrido[(S,S)-N-methanesulfonyl-1,2-diphenylethylene diamine](mesitylene)ruthenium, hydrido[(R,R)-N-methanesulfonyl-1,2-diphenylethylene diamine](mesitylene)ruthenium, hydrido[(S,S)-N-methanesulfonyl-1,2-diphenylethylene diamine](hexamethylbenzene)ruthenium, and hydrido[(R,R)-N-methanesulfonyl-1,2-diphenylethylene diamine](hexamethylbenzene)ruthenium.

Suitable examples of the hydrogen donor include alcohol compounds having a hydrogen atom at the α-position such as methanol, ethanol, 1-propanol, 2-propanol, 1-butanol, sec-butyl alcohol and benzyl alcohol, formic acid and salts thereof; 2-propanol and formic acid are preferred. The hydrogen donor can be used singly or a plurality thereof can be used in combination.

The asymmetric reduction reaction is carried out in the presence or absence of a base. Examples of the base include alkali metal hydroxides such as lithium hydroxide, sodium hydroxide and potassium hydroxide, alkali metal alkoxides such as lithium methoxide, sodium methoxide, sodium ethoxide and potassium isopropoxide and organic amines such as trimethylamine, triethylamine and triisopropylamine. When using a base, it is preferably used in excess, for example, at a molar ratio of 1 to 10,000 times relative to the catalyst. The base can be used singly or a plurality thereof can be used in combination. In general, when an alcohol is used as the hydrogen donor, potassium hydroxide is used at 1 to 10 moles per mole of the catalyst, and when formic acid is used as the hydrogen donor, triethylamine is used in at least an equimolar amount, for example, 1 to 10,000 moles per mole of the catalyst. Furthermore, with regard to the alcohol and the formic acid, it is necessary to use an amount of formic acid sufficient to reduce the ketone substrate. Preferably, it is necessary to use 1 to 10 moles per mole of ketone.

Moreover, the asymmetric reduction reaction may be carried out in the absence of a base when an alcohol compound such as 2-propanol is used as the hydrogen donor.

With regard to preferred combinations of the hydrogen donor and the base, 2-propanol/potassium hydroxide and formic acid/triethylamine can be cited, formic acid/triethylamine being most preferred. When using a combination of formic acid and an amine, a mixture of formic acid and the amine may be prepared in advance or they may be prepared in the reactor. The molar ratio of formic acid to triethylamine (the value of [number of moles of formic acid/number of moles of tertiary amine]) should be optimized by changing the amounts of formic acid and triethylamine added while considering the stability of the carbonyl compound to acid and base.

When an α-nitro ketone or an α-cyano ketone is reduced under the same reaction conditions as those in an example of JP, A, 9-157196 where the molar ratio of formic acid to triethylamine is 2.5, condensation reactions, etc. between the substrate molecules occur, thus causing difficulties such as an inability to obtain the target product, a low yield and the reaction not proceeding, it being therefore necessary to set the molar ratio of formic acid to triethylamine according to the substrate. Such a molar ratio of formic acid to triethylamine is 0.1 to 5.0 and preferably 0.2 to 3.0. In the case of an α-cyano ketone in particular, it is preferably 2.0 or less.

Although the hydrogen donor itself is normally used as the reaction solvent, in order to dissolve the starting material, an aromatic compound such as toluene or xylene, a halide such as dichloromethane or an organic compound such as dimethylsulfoxide (DMSO), dimethylformamide (DMF), tetrahydrofuran (THF) or acetonitrile can be used singly or in combination. In particular, when X in general formula (A) is a nitro group, the addition of dimethylformamide, acetonitrile, etc. as a reaction solvent can enhance the reaction yield, and it is therefore preferable to add a solvent.

The molar ratio (S/C) of the starting material to the compound of a metal belonging to group VIII of the periodic table is usually 10 to 100,000, and preferably 100 to 2,000. The amount of the hydrogen donor relative to the starting material is usually in the range of 1 mole per mole to a large excess (usually 1000 moles per mole); in general, when an alcohol is used as the hydrogen donor, it is used in large excess so as to serve also as a solvent, and when formic acid is used as the hydrogen donor, it is used at a molar ratio in the range of 1 to 20 times. Although the reaction temperature is not particularly limited as long as it is in the range of about −20° C. to 100° C., in order to carry out industrial production it is preferably 10° C. to 50° C. A particularly preferred temperature range is around the room temperature range of 20° C. to 40° C., and this temperature range does not require special equipment, etc. for carrying out the reaction. The reaction pressure is not particularly limited, and usually is 0.5 to 2 atm., it being preferably 1 atm. Although, the reaction time depends on reaction conditions such as the concentration of the reaction substrate, the temperature and the pressure, the reaction is completed in a few minutes to 100 hours. Purification of the product can be carried out by a known method such as column chromatography, distillation or recrystallization.

Step (2) Reduction of Optically Active Nitro Alcohols and Cyano Alcohols

A reaction to obtain an optically active amino alcohol represented by general formula (C) by reducing an optically active nitro alcohol or cyano alcohol represented by general formula (B) can employ a heterogeneous metal catalyst, a metal hydride or a boron hydride compound.

With regard to the heterogeneous metal catalyst, for example, carbon-supported palladium, palladium hydroxide, nickel, platinum, etc. can be used. A reduction reaction can be carried out using the heterogeneous metal catalysts above at 0.01 to 10 (w/w) % and preferably 0.05 to 5 (w/w) %, relative to the nitro alcohol or cyano alcohol represented by general formula (B) with hydrogen at atmospheric pressure to 100 atm and preferably atmospheric pressure to 50 atm.

With regard to the metal hydride, for example, an aluminum hydride such as $LiAlH_4$ or DIBAL (diisobutylaluminum hydride), an alkali metal boron hydride compound such as $LiBH_4$ or $NaBH_4$ or a metal hydride such as calcium hydride or nickel hydride can be used.

With regard to the boron compound, for example, a boron hydride such as 9-BBN (9-borabicyclo[3.3.1]nonane) or a borane ($BH_3$, $BH_3.(CH_3)_2S$ complex, etc.) can be used.

Purification of the optically active amino alcohol thus formed can be carried out by a known method such as column chromatography, distillation or recrystallization.

Among amino alcohols produced by the present invention, optically active β-amino alcohols are useful as, for example, pharmaceutical intermediates for β-adrenergic blockers. Furthermore, among optically active γ-amino alcohols, optically active 3-amino-1-phenylpropanol derived from benzoylacetonitrile is useful as, for example, a pharmaceutical intermediate for fluoxetine, which is useful as an antidepressant.

Synthesis of fluoxetine, tomoxetine, nisoxetine, norfluoxetine or a derivative thereof using an optically active amino alcohol formed above as a starting material can be carried out by a conventionally known synthetic process, for example, according to processes described in Mitchell et al. (Mitchell, D. and Koenig, T. M., Synthetic Communications, 25(8), 1231–1238 (1995)) and Koenig et al. (Koenig, T. M. and Mitchell, D., Tetrahedron Letters, 35(9), 1339–1342 (1994)). When synthesizing fluoxetine, tomoxetine or nisoxetine, the hydroxyl group may be arylated after monomethylating the amino group or the amino group may be monomethylated after arylating the hydroxyl group. When synthesizing norfluoxetine, it can be synthesized by arylating the hydroxyl group.

EXAMPLES

The present invention is explained further in detail below by reference to examples, but it should not be construed as being limited by the examples. In the examples, % ee denotes the percent enantiomeric excess, S/C denotes the molar ratio of substrate to catalyst (molar ratio of substrate to ruthenium) and Tsdpen denotes N-(p-toluenesulfonyl)-1,2-diphenyl-1,2-ethanediamine.

The following equipment was used for the measurements below.
Yield:
 NMR: Model LA400 (400 MHz) (JEOL Ltd.)
 Internal standard: $^1$H-NMR . . . tetramethylsilane
Optical Purity:
 High performance liquid chromatography (HPLC) (Shimadzu Corporation)
Optical Rotation:
 Model DIP-370 digital polarimeter (JASCO Corporation)

Example 1

Production of (S)-3-hydroxy-3-phenylpropanenitrile

A 50 ml Schlenk flask was charged with 7.26 g (50.0 mmol) of benzoylacetonitrile, 18.1 ml (130 mmol) of triethylamine, 5.8 ml (155 mmol) of formic acid, and 31.8 mg (0.05 mmol, S/C=1000) of RuCl[(S,S)-Tsdpen](p-cymene) under an atmosphere of argon, and stirring was carried out at 30° C. for 24 hours. The solution was poured into water and extracted with ether, the organic layer was washed with saturated brine and then dried with anhydrous sodium sulfate, and the solvent was distilled off under vacuum. The crude product so obtained was distilled under vacuum (0.4 mmHg, 145° C.) to give 6.34 g (yield 86%, $^1$H-NMR) of (S)-3-hydroxy-3-phenylpropanenitrile. When this was analyzed using a CHIRALCEL OJ column (manufactured by Daicel Chemical Industries, Ltd., eluant; n-hexane:2-propanol=20:1) it was found that the optical purity was 98% ee.

Examples 2 to 4

The procedure of Example 1 was repeated except that the ratios of formic acid and triethylamine relative to 435 mg (3 mmol) of benzoylacetonitrile were as shown in Table 1. The reaction solution was quantitatively analyzed by $^1$H-NMR, the optical purity was measured by HPLC (CHIRALCEL OJ column), and it was found that (S)-3-hydroxy-3-phenylpropanenitrile was obtained with the yield and the optical purity shown in Table 1.

TABLE 1

|  | Example 2 | Example 3 | Example 4 |
| --- | --- | --- | --- |
| Ketone/formic acid/triethylamine (molar ratio: ketone = 3 mmol) | 1/5.2/2.6 | 1/4.2/2.6 | 1/3.1/2.6 |
| Formic acid/triethylamine (molar ratio) | 2.0 | 1.6 | 1.2 |
| Yield (%) | >99 | >99 | >99 |
| Optical purity (% ee) | 96 | 96 | 96 |

Example 5

Production of (S)-3-amino-1-phenylpropanol

To 10 ml of a THF solution of 1.47 g (10.0 mmol) of the (S)-3-hydroxy-3-phenylpropanenitrile obtained in Example 1, slowly added was 1.23 ml (13.0 mmol) of borane.dimethylsulfide complex. After removing the dimethylsulfide by reducing the pressure, the reaction mixture was refluxed for 2.5 hours. The reaction was stopped by the addition of a methanol/hydrochloric acid solution, and the methanol was distilled off under vacuum. After neutralizing with a 5N aqueous solution of sodium hydroxide, the solvent was distilled off, a further aqueous solution of sodium hydroxide was added to make the reaction solution basic, and this was then extracted with methylene chloride. This methylene chloride solution was dried with anhydrous sodium sulfate, and the solvent was then distilled off under vacuum to give 1.47 g of (S)-3-amino-1-phenylpropanol. The amino group of (S)-3-amino-1-phenylpropanol was monobenzoylated by reaction with benzoyl chloride, and when it was analyzed using a CHIRALCEL OB column (manufactured by Daicel Chemical Industries, Ltd., eluant; n-hexane:2-propanol= 90:10) it was found that the optical purity was 98% ee.

Example 6
Production of Optically Active 3-(2-thienyl)-3-hydroxypropanenitrile A 50 ml Schlenk flask was charged with 4.54 g (30.0 mmol) of 3-(2-thienyl)-3-oxopropanenitrile, 10.88 ml (78 mmol) of triethylamine, 3.51 ml (93 mmol) of formic acid, and 19.1 mg (0.03 mmol, S/C=1000) of RuCl[(S,S)-Tsdpen](p-cymene) under an atmosphere of argon, and stirring was carried out at 30° C. for 24 hours. The reaction solution was poured into water and extracted with ether, and the organic layer was washed with saturated brine and then dried with anhydrous sodium sulfate. After removing the drying agent, the solvent was distilled off, and the oil so obtained was purified by silica gel column chromatography (eluant; n-hexane:ethyl acetate=4:1) to give 4.23 g of optically active 3-(2-thienyl)-3-hydroxypropanenitrile. $^1$H-NMR supported it was the target product and the yield was 92%.

$^1$H-NMR (400 MHz, CDCl$_3$)δ 2.62 (brs, 1H, OH) 2.88 (m, 2H, C$\underline{H}_2$CN) 5.30 (t, J=6.1 Hz, 1H, C$\underline{H}$OH) 6.95–7.45 (m, 3H, aromatic ring protons)

When the optical purity was measured using CHIRALCEL OJ (n-hexane:2-propanol=90:10, 0.5 ml/min, 35° C., 254 nm), it was found to be 98% ee. The optical rotation $[\alpha]_D^{25}$ was −21.8° (c=1.02, EtOH).

Example 7
Production of Optically Active 1-(2-thienyl)-3-aminopropanol

To 10 ml of a THF solution of 1.53 g (10 mmol) of the optically active 3-(2-thienyl)-3-hydroxypropanenitrile obtained in Example 6, slowly added was 1.23 ml (13 mmol) of borane.dimethylsulfide complex. After removing the dimethylsulfide by reducing the pressure, the reaction mixture was refluxed for 2.5 hours. The reaction was stopped by addition of a methanol/hydrochloric acid solution, and the methanol was distilled off under vacuum. After neutralizing with a 5N aqueous solution of sodium hydroxide, the solvent was distilled off, a further aqueous solution of sodium hydroxide was added to make the reaction solution basic, and this was then extracted with methylene chloride. This methylene chloride solution was dried with anhydrous sodium sulfate, and the solvent was then distilled off under vacuum to give 1.28 g (yield 81%, $^1$H-NMR) of optically active 1-(2-thienyl)-3-aminopropanol.

Example 8
Production of (R)-2-nitro-1-phenylethanol

A 20 ml Schlenk flask was charged with 165 mg (1.0 mmol) of benzoylnitromethane, 0.33 ml (2.4 mmol) of triethylamine, 0.23 ml (6.0 mmol) of formic acid, 1 ml of dimethylformamide (DMF), and 3.2 mg (0.005 mmol, S/C=200) of RuCl[(S,S)-Tsdpen](p-cymene) under an atmosphere of argon, and stirring was carried out at 30° C. for 16 hours. When the reaction solution was quantitatively analyzed by $^1$H-NMR, it was found that (R)-2-nitro-1-phenylethanol was obtained in a yield of 90%. This was reduced with 10% Pd/C to (R)-2-amino-1-phenylethanol, the amino group was then monobenzoylated by reaction with benzoyl chloride, and when it was analyzed using a CHIRALCEL OJ column (eluant; n-hexane:2-propanol= 120:5), it was found that the optical purity was 98% ee.

Examples 9 and 10

The procedure of Example 8 was repeated except that RuCl[(S,S)-Tsdpen](p-cymene) was used at S/C=100 relative to benzoylnitromethane, and the reaction solvent was changed as shown in Table 2. When the yield and the optical purity were measured in the same manner as in Example 8, it was found that (R)-2-nitro-1-phenylethanol was obtained with the yields and optical purities shown in Table 2.

TABLE 2

|  | Example 9 | Example 10 |
| --- | --- | --- |
| Reaction solvent | Acetonitrile | Dimethylformamide |
| Yield (%) | 67 | 87 |
| Optical purity (% ee) | 97 | 97 |

Example 11
Production of (R)-2-amino-1-phenylethanol

A recovery flask was charged with 608 mg (3.64 mmol) of (R)-2-nitro-1-phenylethanol obtained under the same reaction conditions as in Example 8, 61 mg of 10% Pd/C, and 3.6 ml of methanol, and stirring was carried out under an atmosphere of hydrogen at atmospheric pressure and 30° C. for 22 hours. After the reaction was completed, the catalyst was filtered off, and the solvent was distilled off under vacuum to give 460 mg (yield 92%, $^1$H-NMR) of (R)-2-amino-1-phenylethanol. The amino group of the (R)-2-amino-1-phenylethanol was monobenzoylated by reaction with benzoyl chloride, and when it was analyzed using a CHIRALCEL OD column (eluant; n-hexane:2-propanol= 120:5) it was found that the optical purity was 98% ee.

Example 12
Production of Optically Active 2-nitro-1-(4-methylphenyl)ethanol

A 50 ml Schlenk flask was charged with 1.075 g (6.0 mmol) of 1-(4-methylphenyl)-2-nitroethanone, 2.01 ml (14.4 mmol) of triethylamine, 1.36 ml (36.0 mmol) of formic acid, 6 ml of dimethylformamide (DMF), and 38.2 mg (0.06 mmol, S/C=100) of RuCl[(S,S)-Tsdpen](p-cymene) under an atmosphere of argon, and stirring was carried out at 30° C. for 16 hours. The reaction solution was poured into water and extracted with ether, and the organic layer was washed with saturated brine and then dried with anhydrous sodium sulfate. After removing the drying agent, the solvent was distilled off, and the oil so obtained was purified by silica gel column chromatography (eluant; n-hexane:ethyl acetate=9:1) to give 0.60 g of optically active 2-nitro-1-(4-methylphenyl)ethanol.

Example 13
Production of Optically Active 2-amino-1-(4-methylphenyl)ethanol

A recovery flask was charged with 470 mg (2.59 mmol) of the optically active 2-nitro-1-(4-methylphenyl)ethanol obtained in Example 12, 47 mg of 10% Pd/C, and 2.6 ml of methanol, and stirring was carried out under an atmosphere of hydrogen at atmospheric pressure and 30° C. for 22 hours. After the reaction was completed, when the catalyst was filtered off and the solvent was distilled off under vacuum, 372 mg (yield 95%, $^1$H-NMR) of white crystals of optically active 2-amino-1-(4-methylphenyl)ethanol was obtained.

Example 14
Production of Optically Active 1-(4-fluorophenyl)-2-nitro Ethanol

A 50 ml Schlenk flask was charged with 1.831 g (10.0 mmol) of 1-(4-fluorophenyl)-2-nitroethanone, 3.35 ml (24.0 mmol) of triethylamine, 2.26 ml (60.0 mmol) of formic acid, 10 ml of dimethylformamide (DMF), and 31.8 mg (0.05 mmol, S/C=200) of RuCl[(S,S)-Tsdpen](p-cymene) under an atmosphere of argon, and stirring was carried out at 30° C. for 16 hours. The reaction solution was poured into water and extracted with ether, and the organic layer was washed with saturated brine and then dried with anhydrous sodium sulfate. After removing the drying agent, the solvent was distilled off, and the oil so obtained was purified by silica gel column chromatography (eluant; n-hexane:ethyl acetate= 9:1) to give 1.48 g of optically active 1-(4-fluorophenyl)-2-nitroethanol. $^1$H-NMR supported it was the target product, and the yield was 80%.

$^1$H-NMR (400 MHz, CDCl$_3$); δ 2.86 (d, J=3.6 Hz, 1H, OH), 4.99 (dd, J=3.0, 13.4 Hz, 1H, C$\underline{H}$HNO$_2$), 4.58 (dd, J=9.5, 13.4 Hz, 1H, CH$\underline{H}$NO$_2$), 5.45 (m, 1H, C$\underline{H}$OH), 7.00–7.25, 7.30–7.50 (m, 4H, aromatic ring protons)

The optical rotation $[\alpha]_D^{25}$ was −19.1° (c=1.04, C$_2$H$_5$OH).

Example 15
Production of Optically Active 2-amino-1-(4-fluorophenyl) Ethanol

A recovery flask was charged with 520 mg (2.81 mmol) of the optically active 1-(4-fluorophenyl)-2-nitroethanol obtained in Example 14, 52 mg of 10% Pd/C, and 2.8 ml of methanol, and stirring was carried out under an atmosphere of hydrogen at atmospheric pressure and 30° C. for 22 hours. After the reaction was completed, the catalyst was filtered off and the solvent was distilled off under vacuum to give 421 mg (yield 97%, $^1$H-NMR) of optically active 2-amino-1-(4-fluorophenyl)ethanol as white crystals. The amino group of the amino alcohol so obtained was monobenzoylated by reaction with benzoyl chloride, and when it was analyzed using a CHIRALCEL OD column (eluant; n-hexane:2-propanol=30:1), it was found that the optical purity was 96% ee.

Effects of the Invention

In accordance with the present invention, optically active amino alcohols, which are important as pharmaceutical intermediates, can be produced efficiently by way of producing optically active nitro alcohols and cyano alcohols with a high reaction yield and high optical purity from nitro ketones and cyano ketones by suppressing side reactions such as condensation reactions between the carbonyl compound molecules and then reducing these intermediates.

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference.

What is claimed is:

1. A process for producing an optically active amino alcohol, comprising:

a step in which a compound represented by general formula (A)

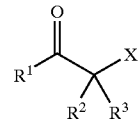

wherein R$^1$ is an aromatic monocyclic or aromatic polycyclic hydrocarbon group, which may have one or more substituents, a saturated or unsaturated aliphatic hydrocarbon or alicyclic hydrocarbon group, which may have one or more substituents, or a heteromonocyclic or heteropolycyclic group, which may have one or more substituents, R$^2$ and R$^3$ each independently denote a hydrogen atom, a halogen atom, a carboxyl group, a hydroxyl group, an alkoxy group, an aromatic monocyclic or aromatic polycyclic hydrocarbon group, which may have one or more substituents, a saturated or unsaturated aliphatic hydrocarbon or alicyclic hydrocarbon group, which may have one or more substituents and which may contain a heteroatom, or a heteromonocyclic or heteropolycyclic group, which may have one or more substituents, any two of R$^1$ to R$^3$ may bond together so as to form a ring, and X denotes a nitro group or a cyano group, is reacted, in the presence or absence of a base, with an optically active nitrogen-containing compound, a compound of a metal belonging to group VIII of the periodic table, and a hydrogen donor so as to obtain a compound represented by general formula (B)

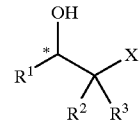

wherein R$^1$, R$^2$, R$^3$, and X are as defined above, and * denotes an asymmetric carbon atom, from the compound represented by general formula (A); and a step in which a compound represented by general formula (C)

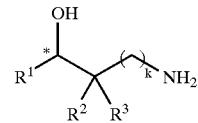

wherein R$^1$, R$^2$, and R$^3$ are as defined above, k denotes an integer of 0 or 1, and * denotes an asymmetric carbon atom, is obtained from the compound represented by general formula (B).

2. The process for producing an optically active amino alcohol according to claim 1 wherein, in the step in which the compound represented by general formula (B) is obtained from the compound represented by general formula (A), the compound represented by general formula (B) is obtained by reacting the compound represented by general formula (A), in the presence or absence of a base, with a hydrogen donor and a complex prepared in advance from an optically active nitrogen-containing compound and a compound of a metal belonging to group VIII of the periodic table.

3. The process for producing an optically active amino alcohol according to either claim 1 or claim 2 wherein the optically active nitrogen-containing compound is a compound represented by general formula (D)

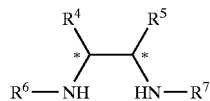

wherein $R^4$ and $R^5$ each independently denote an aromatic monocyclic or aromatic polycyclic hydrocarbon group, which may have one or more substituents, a saturated or unsaturated aliphatic hydrocarbon or alicyclic hydrocarbon group, which may have one or more substituents and which may contain a heteroatom, or a heteromonocyclic or heteropolycyclic group, which may have one or more substituents, $R^4$ and $R^5$ may bond together so as to form a ring, $R^6$ and $R^7$ each independently denote a hydrogen atom, a lower alkyl group, an acyl group, a carbamoyl group, a thioacyl group, a thiocarbamoyl group, an alkylsulfonyl group, or an arylsulfonyl group, and * denotes an asymmetric carbon atom.

4. The process for producing an optically active amino alcohol according to claim 3 wherein the optically active nitrogen-containing compound is a compound represented by general formula (E)

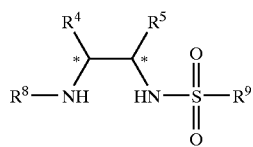

wherein $R^4$ and $R^5$ are as defined above, $R^8$ denotes a hydrogen atom or an alkyl group, $R^9$ denotes an alkyl or aryl group, which may have one or more substituents, and

* denotes an asymmetric carbon atom.)

5. The process for producing an optically active amino alcohol according to claim 4 wherein the optically active nitrogen-containing compound is a compound represented by general formula (F).

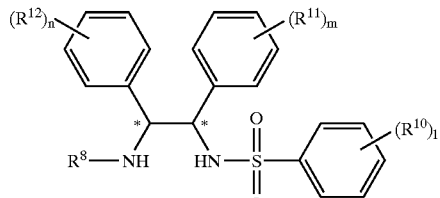

wherein $R^8$ is as defined above, $R^{10}$, $R^{11}$, and $R^{12}$ each independently denote a hydrogen atom, a lower alkyl group, a halogen atom, or a lower alkoxy group, 1, m, and n each independently denote an integer of 1 to 5, and * denotes an asymmetric carbon atom.

6. The process for producing an optically active amino alcohol according to claim 1 wherein the compound of a metal belonging to group VIII of the periodic table is a ruthenium compound.

7. The process for producing an optically active amino alcohol according to claim 1 wherein the hydrogen donor is one or more compounds selected from the group consisting of formic acid, formates, and alcohol compounds, and the base is one or more compounds selected from the group consisting of organic amines, alkali metal hydroxides, and alkali metal alkoxides.

8. The process for producing an optically active amino alcohol according to claim 7 wherein the hydrogen donor is formic acid, and the base is a tertiary amine.

9. The process for producing an optically active amino alcohol according to claim 1 wherein the step in which the compound represented by general formula (C) is obtained from the compound represented by general formula (B) is a reduction step involving a reaction with hydrogen in the presence of a heterogeneous metal catalyst, or a reduction step involving a reaction with a metal hydride or a boron hydride compound.

10. The process for producing an optically active amino alcohol according to claim 1 wherein X is a nitro group, and in the step in which the compound represented by general formula (B) is obtained from the compound represented by general formula (A) a reaction solvent is further added.

11. A process for producing to produce fluoxetine, tomoxetine, nisoxetine, norfluoxetine, or a derivative thereof, comprising producing an optically active amino alcohol according to claim 1.

* * * * *